United States Patent
Altrogge et al.

(10) Patent No.: US 9,284,525 B2
(45) Date of Patent: Mar. 15, 2016

(54) METHOD AND A DEVICE FOR THE ELECTRICAL TREATMENT OF A PLURALITY OF CONTAINERS

(75) Inventors: Ludger Altrogge, Mechernich (DE); Timo Gleissner, Euskirchen (DE); Andreas Heinze, Köln (DE); Herbert Müller-Hartmann, Köln (DE); Andreas Wirth, Weidense (DE)

(73) Assignee: LONZA COLOGNE GMBH, Cologne (DE)

( * ) Notice: Subject to any disclaimer, the term of this patent is extended or adjusted under 35 U.S.C. 154(b) by 282 days.

(21) Appl. No.: 13/145,142
(22) PCT Filed: Jan. 20, 2010
(86) PCT No.: PCT/EP2010/000297
§ 371 (c)(1),
(2), (4) Date: Dec. 2, 2011
(87) PCT Pub. No.: WO2010/083987
PCT Pub. Date: Jul. 29, 2010

(65) Prior Publication Data
US 2012/0067639 A1 Mar. 22, 2012

Related U.S. Application Data

(60) Provisional application No. 61/146,244, filed on Jan. 21, 2009.

(30) Foreign Application Priority Data

Jan. 20, 2009 (EP) .................................. 09000701

(51) Int. Cl.
*C12M 1/42* (2006.01)
*C12M 3/00* (2006.01)
(Continued)

(52) U.S. Cl.
CPC ............... *C12M 35/02* (2013.01); *C12M 23/44* (2013.01); *Y10T 29/49117* (2015.01)

(58) Field of Classification Search
CPC ............................. C12M 23/44; C12M 35/02
USPC ........................................... 435/283.1–309.4
See application file for complete search history.

(56) References Cited

U.S. PATENT DOCUMENTS 5,183,744 A  2/1993 Kawamura et al.
6,150,148 A  11/2000 Nanda et al.
(Continued)

FOREIGN PATENT DOCUMENTS

EP  0338667 A1  10/1989
EP  1577378 A   9/2005
(Continued)

OTHER PUBLICATIONS

Database WPI, Week 200437, Thomson Scientific, London; AN 2004-0396004, XP002626706.
International Preliminary Report on Patentability Chapter I for PCT/EP2010/00297 (Jul. 26, 2011).

*Primary Examiner* — Nathan Bowers
*Assistant Examiner* — Lydia Edwards
(74) *Attorney, Agent, or Firm* — Joyce von Natzmer; Agris & von Natzmer LLP

(57) ABSTRACT

The invention relates to a method for the application of at least one voltage pulse to at least two containers fitted with electrodes, by means of which at least one voltage pulse is applied to at least one container, while at least one other container is subjected to a preparation or a post-processing. According to the invention the method comprises mutual exchange of the respective positions of the container to which a voltage pulse has already been applied and the further container. Furthermore, the invention relates to a device (1) for making electrical contact with at least one container fitted with electrodes, with at least one receptacle (3, 7) upon which at least one container can be set, and with at least one contact appliance (8) for making contact with the electrodes of the container. According to the invention at least two receptacles (3, 7) are provided, wherein one receptacle (7) is located at or inside the contact appliance (8), and wherein both receptacles (3, 7) and/or the contact appliance (8) can be moved such that after completion of the movement the other receptacle (3) is located at or inside the contact appliance (8).

14 Claims, 7 Drawing Sheets

(51) Int. Cl.
*C12M 1/36* (2006.01)
*C12M 1/38* (2006.01)
*C12M 1/00* (2006.01)

(56) References Cited

U.S. PATENT DOCUMENTS

| | | |
|---|---|---|
| 6,878,538 B1 | 4/2005 | Walters et al. |
| 8,101,401 B2 | 1/2012 | Mueller-Hartmann et al. |
| 2003/0129716 A1 | 7/2003 | Ragsdale et al. |
| 2004/0262162 A1* | 12/2004 | Roach et al. .................. 204/600 |
| 2006/0121612 A1* | 6/2006 | Tajima et al. ................. 435/459 |
| 2006/0246572 A1 | 11/2006 | Ragsdale et al. |
| 2006/0249558 A1* | 11/2006 | Roach et al. .................. 228/101 |
| 2008/0081372 A1* | 4/2008 | Huang ........................... 435/440 |
| 2009/0042739 A1* | 2/2009 | Okano et al. ..................... 506/12 |

FOREIGN PATENT DOCUMENTS

| | | |
|---|---|---|
| JP | 2003272685 A | 9/2003 |
| JP | 2004147517 | 5/2004 |
| WO | 0002038 A1 | 1/2000 |
| WO | 03/057819 A | 7/2003 |
| WO | 03001889 A2 | 9/2003 |
| WO | 03/095019 A2 | 11/2003 |
| WO | 2005/044983 A | 5/2005 |
| WO | 2007/056512 A | 5/2007 |
| WO | 2007/094947 A | 8/2007 |
| WO | 2008036840 A2 | 3/2008 |
| WO | 2008057111 A2 | 5/2008 |
| WO | 2009/123564 A1 | 10/2009 |

* cited by examiner

METHOD AND A DEVICE FOR THE ELECTRICAL TREATMENT OF A PLURALITY OF CONTAINERS

This is the U.S. national stage of International application PCT/EP2010/000297, filed Jan. 20, 2010 designating the United States, claiming priority to European patent application no. EP 09000701.4, filed Jan. 20, 2011 and the benefit of US provisional patent application no. US 61/146,244, filed Jan. 21, 2009.

The invention relates to a method for the application of at least one voltage pulse to at least two containers fitted with electrodes, in which at least one voltage pulse is applied to at least one container, while at least one other container is subjected to a preparation or a post-processing. The invention further relates to a device for making electrical contact with at least one container fitted with electrodes, with at least one receptacle upon which at least one container can be set, and with at least one contact appliance for making contact with the electrodes of the container.

Containers fitted with electrodes are used in particular in applications in which an electrical voltage pulse must be applied to the reaction batch, such as, for example, the electroporation, electrofusion and electrostimulation of living cells. Such containers can also have a plurality of reaction volumes, while each reaction volume can be fitted with electrodes. As a rule these containers are designated as multi-hole plates, microtiter plates or multi-wells. They are primarily used in biochemical and pharmaceutical applications, in which a multiplicity of reaction batches must be tested simultaneously. In such circumstances one can discern the desire to make available as large a number of reaction volumes as possible, 384, for example, in particular in HT analyses (HT=high throughput), since the aim here is to test a large number of samples in the shortest possible time.

The containers of known art usually consist of a plurality of reaction volumes, each of which has two electrodes, which are in contact with the reaction batch, for example a cell suspension, in the reaction volume. When an electrical voltage is applied, the two electrodes of a reaction volume generate an electrical field in the interior of the reaction volume, while with direct current, for example, they have different polarities and/or potentials. Here the electrodes of the same polarity, i.e. for example all the cathodes and/or all the anodes, of various reaction volumes are either integrally designed or are electrically coupled with one another, so that they can be connected via a common electrical contact with the voltage source.

The application of voltage pulses to the reaction volumes of such containers takes place by means of particular circuit arrangements, which comprise one or two storage appliance(s) for the storage of electrical charge. In each case the storage appliances take the form of capacitors, which are charged up to a predetermined electrical voltage and by means of systematic discharge can deliver defined voltage pulses. The storage appliances are connected with electrical switches, preferably power semiconductors, via which the systematic discharge of the storage appliances is applied. The use of two storage appliances enables the delivery of two voltage pulses, either rapidly following one another or merging one into another, which can be of advantage in the electroporation of particular cell types. Contact pins serve as a rule for making electrical contact with the electrodes of the containers; the pins are arranged on arms or plates and are brought into contact with the electrodes manually or automatically.

From EP-A-1 577 378 a method and a device are of known art for making contact with a container consisting of a plurality of reaction volumes, for example a microtiter plate with 96 reaction volumes. The device has a housing in which is arranged a contact appliance in the form of a plate, on which the contact means in the form of pins are attached. The contact appliance with the contact means serves to provide electrical contact with the electrodes of the container and can be moved vertically. The device further comprises a receptacle in the form of a table, onto which the container can be set and which can be moved horizontally. If a container is set upon the receptacle, the receptacle can be traversed through the housing opening into the interior of the housing. Thereupon the contact appliance moves vertically from below in the direction of the container until the contact means project through holes in the receptacle and make contact with the electrodes of the container, The overall time of a treatment cycle plays a decisive role in high throughput methods in particular, since cells only live for a limited process time. The resultant process time should therefore be as short as possible. In the high throughput methods of known art the containers are delivered with the reaction volumes pre-filled by a robot, and after the electrical treatment are further processed by this robot. In such circumstances the robot must wait during the treatment of one container, so as then to exchange the container for the next container to be treated, while no container can be subjected to the electrical treatment during this time.

The process time per cycle ($T_p$ =preparation (V) +electrical treatment (B) +post-processing (N)) is therefore significantly dependent on the time (V+N) that is required for the exchange of the containers between two treatments (B) and cannot be executed in parallel of the treatments (B).

It is the object of the invention to provide a method and a device for making electrical contact with at least two containers with a shortened process time.

The object is achieved according to the invention by means of a method of the type cited in the introduction, which comprises the following steps:
a) Preparation of at least one container;
b) Application of at least one voltage pulse to this container, and simultaneously the preparation of at least one further container;
c) Mutual exchange of the respective positions of the container to which a voltage pulse has already been applied, and the further container;
d) Application of at least one voltage pulse to the further container, and simultaneously post-processing of the container to which at least one voltage pulse has been applied, and also preparation of at least one next container.

By this means, in which at least one container is subjected to the electrical treatment, and simultaneously at least one further container is receiving pre- or post-processing, the overall process time can be significantly reduced. That is to say, while the container is subjected to the electrical treatment a robot can remove the container already treated and prepare the next container to be treated. By the method according to the invention the process time per cycle ($T_P$) is therefore reduced by the waiting times and the operating times, so that the overall throughput can be significantly increased.

According to the invention the cycles are nested inside one another such that the process time per cycle ($T_P$) is either B or V+N, depending on which time is the longer. The method according to the invention can be executed with at lest two containers, in particular, also, with more than three containers. In the simplest case the method according to the invention can be implemented, for example, by means of a turntable with two positions.

In the context of the invention a mutual exchange of the respective positions of the containers signifies that the positions of the containers are altered relative to one another, or relative to other components of a device for execution of the method according to the invention, for example a device delivering the voltage pulse. That is to say, either the containers are moved relative to one another, and/or the other components are moved relative to the containers, in which case the containers need not be moved.

The steps b) to d) are preferably multiply repeated, the method being terminated as soon as the voltage pulse or pulses have been applied to all the containers to be treated.

In an advantageous embodiment of the method according to be invention provision is made in each case that a plurality of voltage pulses are applied to the containers during the steps b) and d). This is in particular necessary if containers with a plurality of reaction volumes, in particular 384 reaction volumes, must be treated. Since in this case the treatment of the container requires a longer time it is of particular advantage that the preparation of the next container takes place simultaneously, so that even in applications in which very many samples must be treated the process time can be kept relatively short.

The preparation of the containers during the steps a), b) and d) preferably comprises the delivery of the containers, and/or the post-processing of the container during step d) preferably comprises the removal of the container.

The exchange of the positions of the containers during step c) can, for example, take place such that the containers are mutually exchanged. Simultaneously or alternatively the exchange of the positions of the containers during step c) can also take place such that a device delivering the voltage pulse is moved into the respectively other position. Here the exchange of the positions can, for example, take place by means of a rotational movement. In particular the movements of the containers can in such circumstances be coupled, i.e. can take place simultaneously. Alternatively the exchange of the positions can take place by means of a linear movement. In particular the movements of the containers can in such circumstances be decoupled, i.e. can take place, at least partly, one after another.

In a particularly advantageous embodiment of the method according to the invention provision is made that contact is made with the electrodes of the containers during the steps b) and d) by means of at least one contact appliance, the contact appliance essentially being moved approximately parallel to the plane of contact, preferably horizontally, above the respective container. The electrodes of a container can thus be traversed one after another by a contact appliance, the contact appliance preferably travelling in a stepwise manner above the container.

In a particularly advantageous embodiment of the method according to the invention provision is made that contact is made with the electrodes of the containers during the steps b) and d) by means of at least one contact appliance fitted with at least one contact element, the contact element essentially being moved approximately at right-angles to the plane of contact, preferably vertically, to make the contact. The contact appliance can therefore, for example, travel horizontally over the container, the electrical contact then being made, with the contact appliance stationary, by means of a vertical movement of the contact means in the direction of the electrodes.

The object is further achieved by means of a device of the type cited in the introduction, in which at least two receptacles are provided, one receptacle being located at or inside the contact appliance, while both receptacles and/or the contact appliance can be moved such that after completion of the movement the other receptacle is located at or inside the contact appliance. According to the invention the receptacles with the containers can be moved relative to the contact appliance such that they can exchange their positions. By this means it is, for example, made possible to move away from the contact appliance a receptacle carrying a container with which electrical contact has already been made, i.e. a container that has already been treated, and simultaneously to move into the contact appliance a receptacle carrying a container with which electrical contact is yet to be made, i.e. a container that is yet to be treated. Exchanging the positions of the receptacles represents a very fast facility for making electrical contact with a container, i.e. for treating a container, for the predominant part of the process time, while simultaneously preparing and/or post-processing at least one other container. While therefore contact is made with the electrodes of at least one container by the contact appliance, at least one other receptacle is freely accessible such that one container can be withdrawn and the next container queuing for treatment can be set upon the receptacle. The device according to the invention is therefore very fast and can process many containers with high throughput rates.

The receptacles can, for example, be arranged on a moveable plate. The moveable plate can preferably be moved in a rotary manner, and can be a turntable, for example. Alternatively the moveable plate can, however, also be moved linearly.

In a particularly advantageous embodiment of the device according to the invention provision is made that a least one receptacle is arranged below the contact appliance, so that contact can be made with the electrodes of a container arranged on the receptacle from above. Alternatively the receptacle can also be arranged above the contact appliance, in particular in circumstances in which contact can only be made with the containers from below.

The contact appliance is preferably arranged inside a housing, so that there is no risk of injury to the operator(s) as a result of the electrical voltage pulses. Here at least one receptacle is preferably arranged inside the housing and at least one other receptacle is preferably arranged outside the housing, so that the other receptacle remains freely accessible. If the receptacles are arranged on a moveable plate, one part of the moveable plate should in such circumstances be arranged inside the housing, and another part of the moveable plate outside the housing.

In an alternative form of embodiment of the device according to the invention the contact appliance can be moved back and forth between the receptacles, so that the positions of the receptacles relative to the contact appliance can rapidly be exchanged one for another in the context of the invention.

The invention relates also to a method for making electrical contact with at least one container, which comprises at least two reaction volumes fitted in each case with at least one electrode, contact being made sequentially with the electrodes of the different reaction volumes. Electrical contact with the electrodes of the reaction volumes to be treated is therefore made according to the invention sequentially and not simultaneously. This advantageous method enables the mechanical loading caused by contact to be significantly reduced in an advantageous manner for the container, and also for the receptacle and the contact device, since contact is only ever made simultaneously with a fraction of the electrodes of one container. In the event that contact was being made simultaneously with all electrodes of the container with which contact was to be made, the sum of all forces acting on the container would in fact lead to a high mechanical loading. The small number of contact means necessary to make the electrical contact also has the advantage that the risk of failure and also the costs for the contact appliance are significantly reduced.

In an advantageous embodiment of the method according to the invention provision is made that a contact appliance for making electrical contact with the electrodes moves approximately parallel to at least one plane of contact and electrical contact is then made with the electrodes. This advantageous method enables the rapid traverse of the surface, i.e. of the electrodes of a container, while the electrical contact can be made, for example, by means of a movement of the contact appliance, or of a part of the contact appliance in the direction of the container that is as rapid and short as possible.

In a further advantageous embodiment of the method according to the invention provision is made that the contact appliance is essentially moved approximately parallel to the plane of contact, preferably horizontally, above the container.

Electrical contact is then preferably made by a movement of at least one part of the contact appliance essentially running approximately at right-angles to the plane of contact, preferably vertically.

In a particularly advantageous embodiment of the method according to the invention provision is made that the contact pressure, with which contact is made with the electrodes, is limited. This can take place electronically, and/or by a reduction of the points of contact. Moreover sprung contact means can be used.

For the reconciliation of tolerances of the contact means it can be necessary to use sprung contact means, for example contact pins with a sprung head. However, the sum of all the necessary contact means with their respective spring forces leads to a high contact force in the event of contact being made with all electrodes of a container with which contact is to be made, independently of the contact appliance.

In order to minimise the process time contact is preferably made simultaneously with a plurality of electrodes, particularly preferably with the electrodes of at least two reaction volumes. In this case the mechanical loading for the receiving unit and the container should be reduced, in particular if contact must be made with very many electrodes simultaneously, for example when using 96 or 384-well plates in a high throughput method. Moreover the high number of contact needles required also signifies an increased risk of failure and also not insignificant costs for the contact appliance. These problems can be solved by making sequential contact with individual groups of reaction volumes, i. e. with the various electrodes of a container, by means of a traversable contact appliance. In particular contact can also be made simultaneously with the electrodes of one or a plurality of rows of reaction volumes, preferably two rows, and contact can be made with various rows, or groups of rows, of reaction volumes sequentially. If therefore the container has a plurality of reaction volumes with in each case at least one electrode, individual groups of reaction volumes being determined, and contact being made with the electrodes of the reaction volumes of one group simultaneously, and with the electrodes of the reaction volumes of various groups sequentially, then the contact pressure and thus the mechanical loading for the device can effectively be reduced.

The invention further relates to a device for making electrical contact with at least one container, which comprises at least two reaction volumes fitted with at least one electrode in each case, at least one contact appliance being provided, comprising at least one contact unit that has contact means for making contact with the electrodes, and the number of contact units being smaller than the number of reaction volumes, one contact unit having contact means for making contact with the electrodes of at least two reaction volumes. The sum of the contact forces of all the contact means necessary for making electrical contact would, in the event of contact being made with all electrodes of the container with which contact is to be made, lead collectively to a very high contact pressure. The mechanical loading for the receptacle, the contact appliance and the container is therefore reduced according to the invention in that the number of contact units, and with that also the number of contact means, is smaller than the number of reaction volumes. The small number of contact means also has the advantage that the risk of failure and also the costs for the contact appliance are significantly reduced.

The contact appliance is preferably designed as a type of support, in particular as a type of bridge and/or slide, and can essentially be moved approximately parallel to the plane of contact, preferably horizontally.

In an advantageous embodiment of the invention provision is made that at least one part of the contact appliance of the device according to the invention can essentially be moved approximately at right-angles to the plane of contact, preferably vertically. This part of the contact appliance preferably comprises the contact unit and/or the contact means, by means of which contact is made with the electrodes of the containers.

At least two contact units preferably comprise at least one common contact element, so that in an advantageous manner contact can be made with containers that comprise reaction volumes that have at least partly common and/or electrically coupled electrodes.

The contact appliance can therefore comprise contact means that are preferably contact pins or needles. The contact means can be supported in a sprung manner.

In an advantageous embodiment of the invention provision is also made that a plurality of contact units are arranged in at least one row on the contact appliance. In such circumstances at least three rows of contact means are provided, so that the contact units must be arranged on the contact appliance such that at least three rows of contact means can be arranged on the contact appliance. Here the contact means can also be arranged in the form of a zig-zag.

In a further advantageous embodiment of the invention provision is made that the contact appliance is attached inside an attachment device in the form of a type of frame, which preferably can essentially be moved approximately at right-angles to the plane of contact, in particular vertically.

The contact appliance can essentially be moved, supported on guide elements, approximately parallel to the plane of contact, preferably horizontally.

The invention relates also to a method for making electrical contact with at least one container fitted with electrodes, in which the container is cooled by a cooling appliance, the container being pressed approximately evenly onto the cooling appliance. By means of the even pressure an even, effective and rapid transfer of heat from the electrodes and/or from the surface of the container to the cooling appliance is ensured.

The pressure with which the container is pressed onto the cooling appliance is preferably exerted, at least partly, onto the edges of the container. Additionally, or alternatively, the pressure with which the container is pressed onto the cooling appliance is also exerted, at least partly, onto the electrodes of the container, for example by the contact means. Here the container should be pressed onto the cooling appliance such that air located between the container and the cooling appliance is to a large extent displaced.

The method according to the invention is particularly suitable for use in the electrical treatment of containers with a plurality of reaction volumes, 384 reaction volumes for example.

The invention relates also to a device for making electrical contact with at least one container fitted with electrodes, with at least one receptacle upon which at least one container can be set, the receptacle being fitted with a cooling appliance.

Here the cooling appliance preferably comprises at least one Peltier element. Alternatively, or additionally, the cooling appliance can, however, also comprise at least one cooling body, and/or cold store, and/or at least one ventilator.

In an advantageous embodiment of the invention the device according to the invention can comprise at least one pressure application appliance, which presses the container onto the receptacle and/or the cooling appliance. The pressure application appliance can be designed in the form of a frame and can be set upon at least one part of the edge of the container.

In a particularly advantageous embodiment of the invention provision is made that the pressure application appliance is an electrical contact appliance.

The container can comprise a plurality of reaction volumes, preferably 96 or 384 reaction volumes.

The invention is elucidated in more detail in an exemplary manner in what follows with the aid of the figures.

Figure 1:
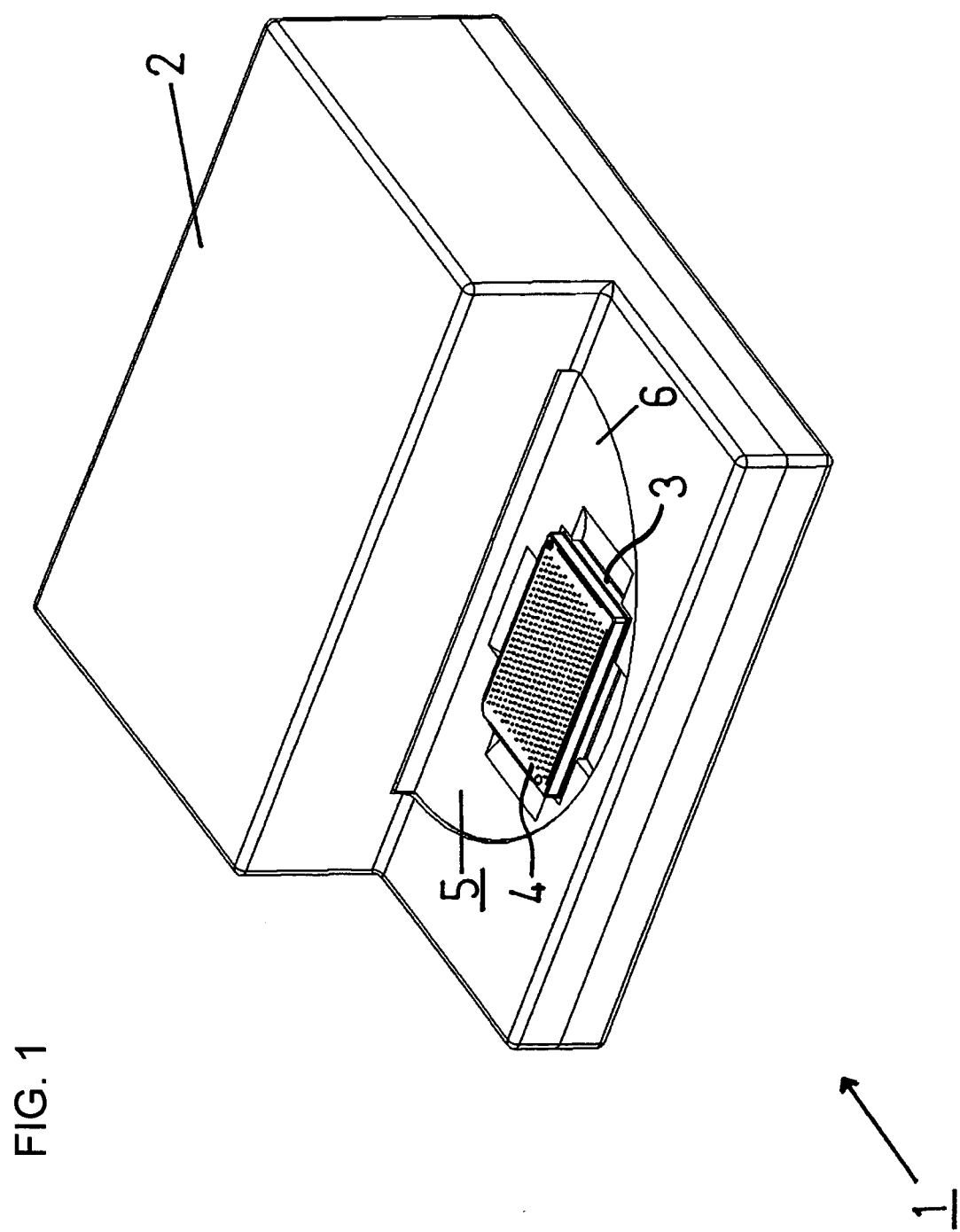
FIG. 1 shows a perspective representation of a form of embodiment of a device according to the invention with housing and container.

FIG. 1 shows a perspective representation of a particularly advantageous form of embodiment of a device according to the invention. The device 1 has a housing 2, in which is arranged a receptacle, not visible here, below a contact appliance, also not visible. The device 1 also comprises a further receptacle 3, upon which a container 4 is set. In this example of embodiment the container 4 takes the form of a microtiter plate with 384 reaction volumes, i.e. a so-called 384-well plate. Alternatively it could, however, also take the form of a microtiter plate with less or more reaction volumes, or another container with at least one reaction volume. The receptacle 3 is arranged on a moveable plate 5, which in this form of embodiment is designed in the form of a turntable 6. Since the non-visible receptacle is also arranged on the turntable 6, the positions of the two receptacles of the device 1 according to the invention can be exchanged by means of a simple rotation of the turntable 6. If therefore the container on the non-visible receptacle inside the housing 2 is subjected to an electrical treatment by the application of at least one voltage pulse to one or a plurality of reaction volumes, an already treated container can thus simultaneously be taken from the receptacle 3 located outside the housing and a further, yet to be treated container, here the container 4, can then be set upon the receptacle 3.

By means of the rotary movement of the turntable 6 the previously electrically treated container can be exchanged with the container that is yet to be treated.

Figure 2:
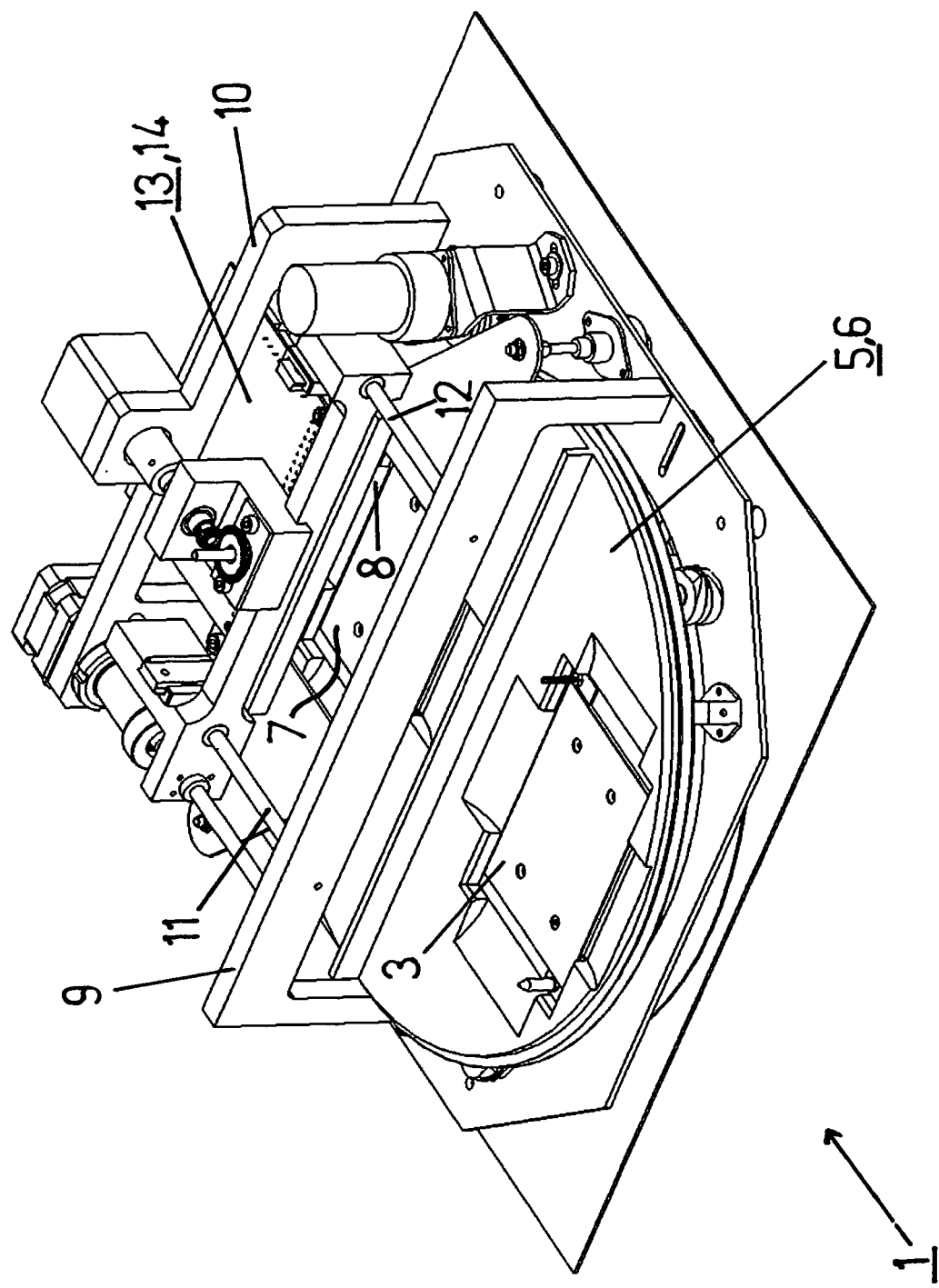
FIG. 2 shows a perspective representation of the device according to the invention as per FIG. 1 without housing or container.

FIG. 2 shows a perspective representation of the form of embodiment as per FIG. 1 without housing or container. The device 1 comprises the moveable plate 5, which is designed in the form of the turntable 6. Two receptacles 3, 7 are arranged on the turntable 6. The receptacle 7 is arranged below a contact appliance 8. The contact appliance 8 here has non-visible contact means, which can make contact with the electrodes of the containers that can be set upon the receptacles 3, 7. The contact appliance 8 is arranged below a distribution appliance 13, which in this example of embodiment comprises a cover plate 14 and switching elements arranged above the latter, preferably relays (not represented). With the aid of the switching elements, or relays, the voltage pulses are distributed to the respective contact means. Since both receptacles 3, 7 are arranged on the turntable 6, the positions of the two receptacles 3, 7 can be exchanged one for another by means of a simple rotary movement, i.e. a rotation, of the turntable 6. If therefore a container on the receptacle 7 is subjected to an electrical treatment by the application of at least one voltage pulse to the reaction volumes of this container, an already treated container can thus simultaneously be taken from the receptacle 3 located outside the housing and a further, yet to be treated container can then be set upon the receptacle 3. By the rotation of the turntable 6 the previously electrically treated container can be exchanged for the container that is yet to be treated. In this example of embodiment the contact appliance 8 is designed as a type of slide and/or bridge, and is supported on fixed yokes 9, 10 such that it can move horizontally on rails 11, 12. The contact appliance 8 can be moved parallel to the surface of the container, i.e. parallel to the plane of contact. The contact appliance 8 can thus, for example, travel horizontally, preferably in a stepwise manner, over the receptacle 7, i. e. over the container that is located on the latter, enabling the electrical contact then to be made, with the contact appliance 8 stationary, by means of a vertical movement of at least one contact unit, i.e. the contact means, and/or the whole contact appliance 8 in the direction of the electrodes of the container.

Figure 3:
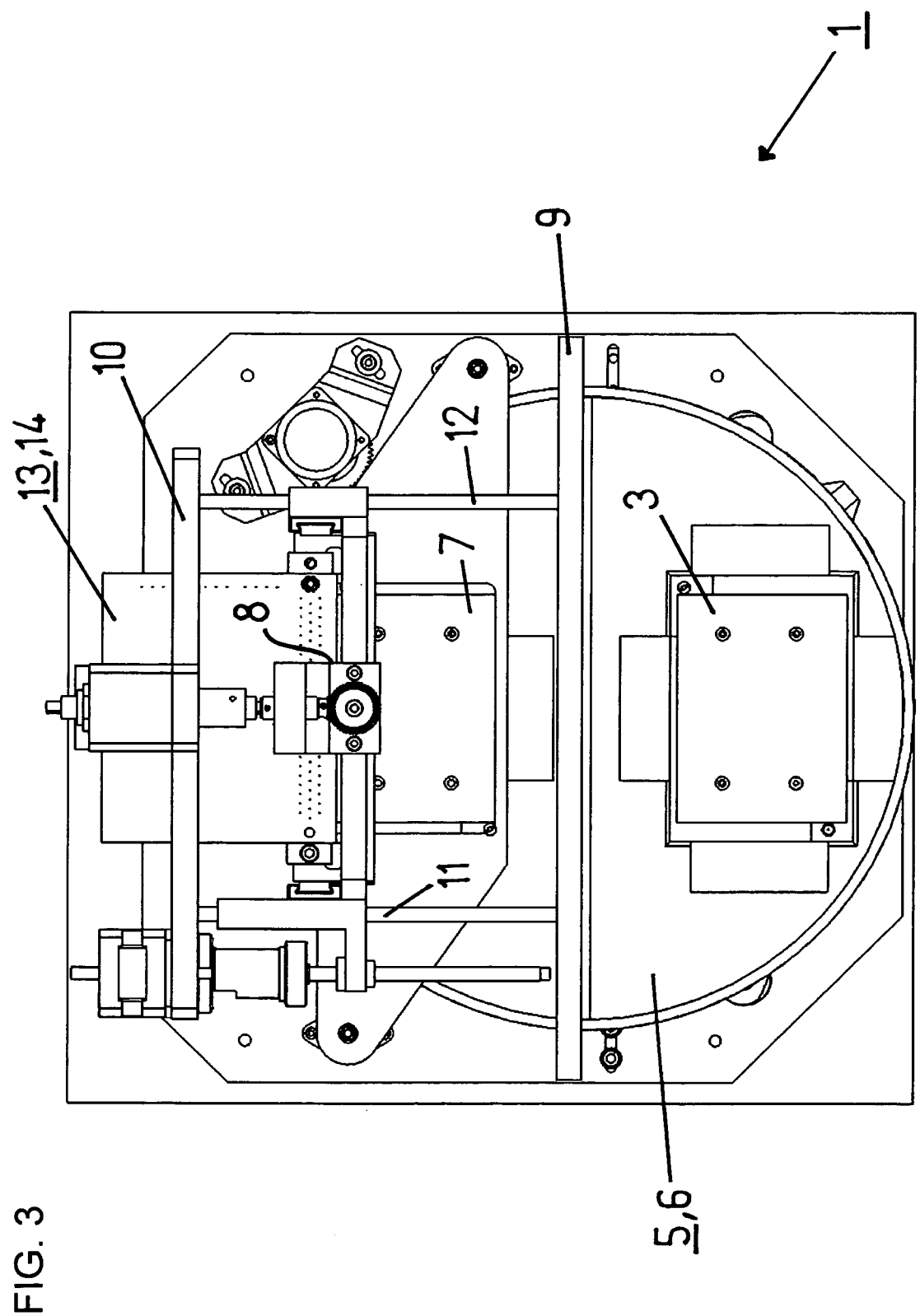
FIG. 3 shows a plan view onto the device according to the invention as per FIG. 2.

FIG. 3 shows a plan view onto the device according to the invention as per FIG. 2. In this representation it becomes clear that the positions of the receptacles 3, 7 can be exchanged one for another by a simple rotary movement of the moveable plate 5, i.e. in this example of embodiment by a rotation of the turntable 6. By means of the rotary movement of the moveable plate 5 the receptacle 7 arranged at or partly below the contact appliance 8 can in a simple manner be moved very rapidly away from the contact appliance 8, in the direction of the current position of the receptacle 3 outside the housing, not represented here. Since the movements of the two receptacles 3, 7 are coupled, the receptacle 3 would in this case be transported into the housing in the direction of the contact appliance 8. After completion of the rotary movement, i.e. preferably after a rotation through 180°, the receptacle 3 would then be arranged at or partly below the contact appliance 8, while the receptacle 7 would be located outside the housing. Since for example in the case of electrotransfections in high throughput methods (high throughput screening) the overall time of a transfection cycle plays a decisive role, because the cells only live for a limited process time, the method and/or the device according to the invention is particularly advantageous. By the method according to the invention with the aid of the device according to the invention the process time is in fact reduced by the waiting times and the operating times, and thus the throughput is significantly increased. In high throughput transfections the microtiter plates are delivered with the reaction volumes pre-filled by a robot, and after the transfection are further processed by this robot. That is to say, while the electrical treatment is executed inside the housing, outside a robot can according to the invention remove the previous container already treated and prepare the new container. Therefore no time is lost in the preparation and post-processing of the containers between the electrical treatments, so that the process time as a whole can be significantly reduced. During the electrical treatment the contact appliance 8 arranged below the distribution appliance 13 is here moved horizontally, i.e. parallel to the plane of contact, over the container that is located on the receptacle 7. Here the container is preferably traversed in a stepwise manner, wherein the contact appliance designed in the form of a bridge is guided along the rails 11, 12. If the contact appliance has reached the desired position above the container, i.e. above the reaction volumes to be treated, electrical contact can be made between the contact means and the electrodes. After the voltage pulse(s) have been applied to the appropriate reaction volumes, the contact between the contact means and the electrodes is broken and the contact appliance 8 is then moved into the next position, where the next reaction volumes are then treated. These processes can be repeated until all desired reaction volumes of the container have been treated. The containers are then exchanged one for another as described above.

Figure 4:
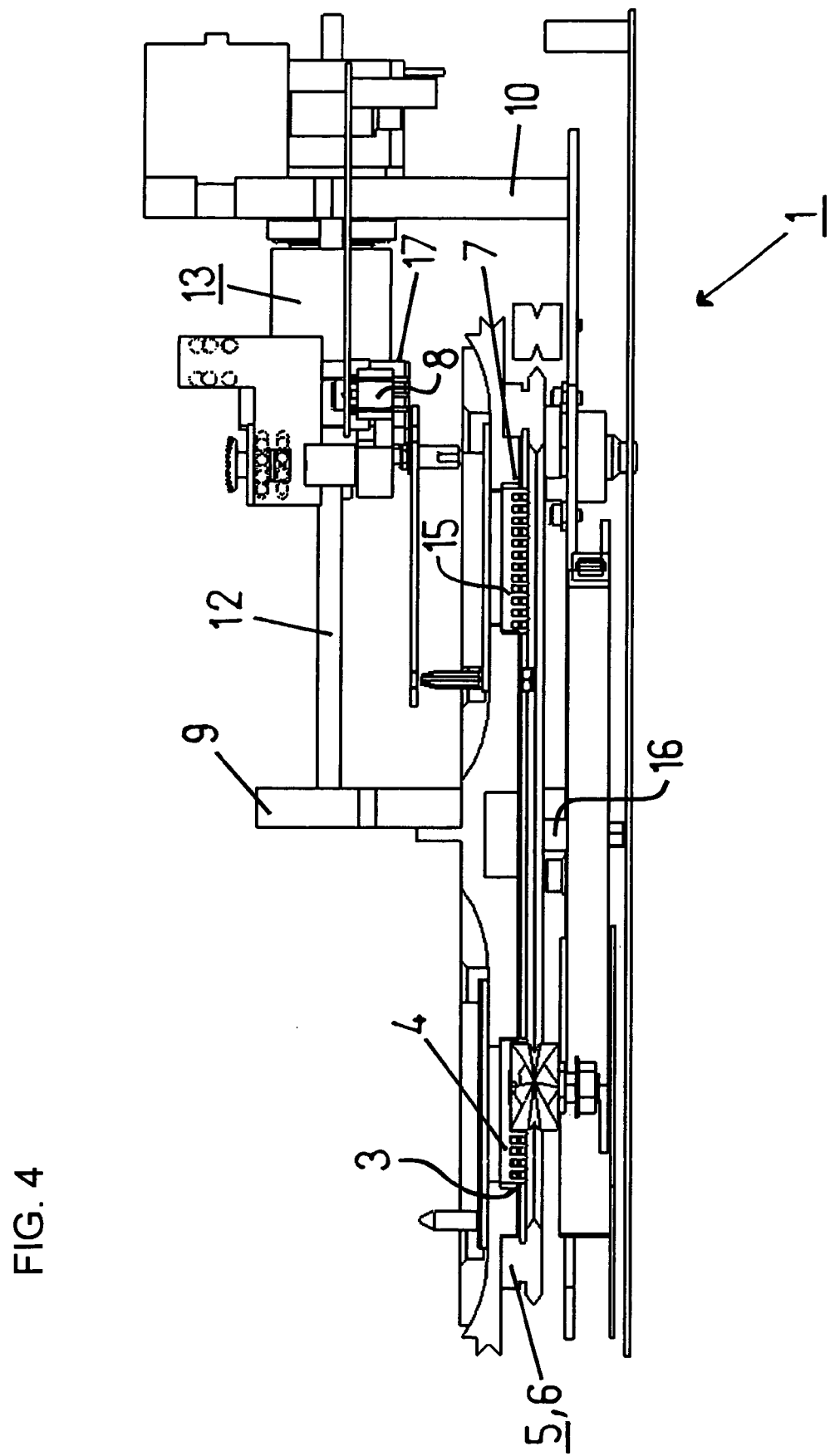
FIG. 4 shows a side view of the device according to the invention as per FIG. 2.

FIG. 4 shows a side view of the form of embodiment as per FIG. 2. Here it is clear that the moveable plate 5 can perform a rotary i.e. circular, movement about the axis 16, so that the positions of the receptacles 3, 7 can be exchanged one for another. Furthermore it is clear that two containers 4, 15 are here arranged on the moveable plate 5. The container 4 is set upon the receptacle 3 outside the housing, not represented here, while the container 15 is set upon the receptacle 7 inside the housing. The container 15 is therefore arranged at the contact appliance 8, which can be moved horizontally along the rail 12 over the container 15. This movement and the making of the electrical contact between the contact means 17 of the contact appliance 8 and the electrodes of the container 15 are described in more detail with the aid of FIG. 5.

Figure 5:
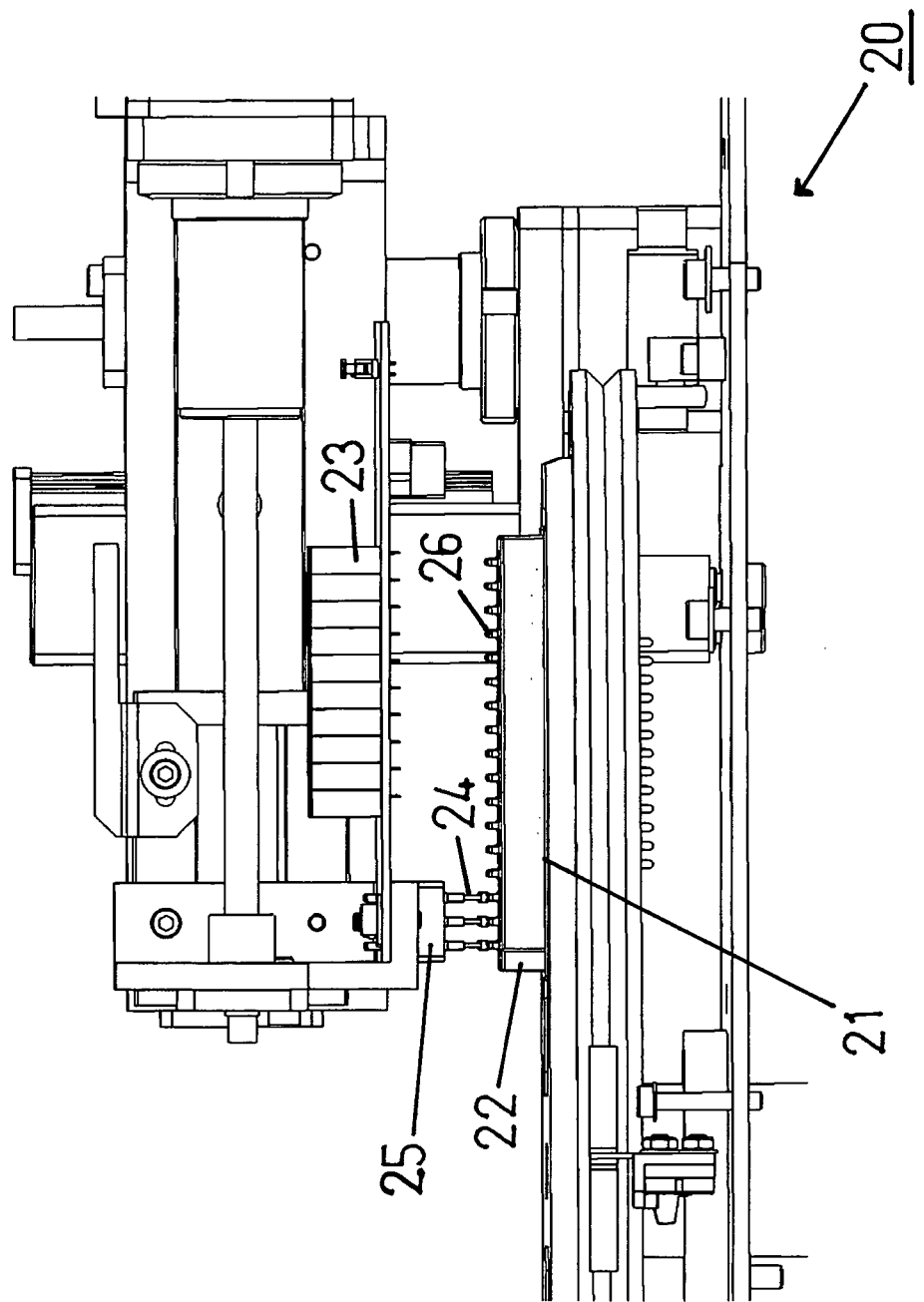
FIG. 5 shows a side view of a form of embodiment of a device according to the invention with a container and a contact appliance.

FIG. 5 shows a side view of a form of embodiment of a device according to the invention with a container and a contact appliance. The device 20 comprises a receptacle 21, on which a container 22 is arranged. The container 22 comprises a plurality of reaction volumes, each of which is fitted with two electrodes, with which electrical contact can be made from above via contact elements 26 projecting upwards from the electrodes. The contact takes place by means of the contact means 24, which are attached to the underside of a contact appliance 25, and in this example are designed in the form of pins. The contact appliance 25 is moved horizontally, i.e. parallel to the plane of contact, over the container 22. Here the container is preferably traversed in a stepwise manner. If the contact appliance 25 has reached the desired position above the container 22, i.e. above the reaction volumes to be treated, electrical contact can be made between the contact means 24 and the contact elements 26 of the electrodes of the respective reaction volumes. Here contact is made by means of a vertical movement, i.e. a lowering of the contact appliance 25 in the direction of the container 22. For the reconciliation of tolerances of the contact means it is advantageous to use contact means with a sprung head. However the sum of all the necessary contact means with their respective spring forces would lead to a high contact force in the event of contact being made with all electrodes of the container with which contact is to be made, independently of the contact appliance. The mechanical loading for the receptacle and the container is significantly reduced according to the invention, in that contact is only ever made with a fraction of the electrodes of a container simultaneously. The contact appliance 25 is therefore designed in the form of a bridge and has on its underside three rows of contact means (of which here only the forwardmost contact means 24 are visible), whose total number is less than the number of reaction volumes. The small number of contact means necessary also has the advantage that the risk of failure and also the costs for the contact appliance are significantly reduced. According to the invention sequential contact therefore takes place in an advantageous manner with in each case a fraction of the container 22, preferably with two rows of reaction volumes, by means of the traversable contact appliance 25. Because of the form of the container 22, which in this example of embodiment is a microtiter plate, an arrangement of the contact means 24 in rows is here advantageous. After the voltage pulse(s) have been applied to the appropriate reaction volumes, the contact between the contact means 24 and the contact elements 26 of the electrodes is broken and the contact appliance 25 is then moved into the next position, where the next reaction volumes are then treated. These processes can be repeated until all desired reaction volumes of the container 22 have been treated. Here the voltage pulses are distributed to the individual contact means 24 by means of a distribution appliance 23, which can, for example, comprise individual relays.

Figure 6:
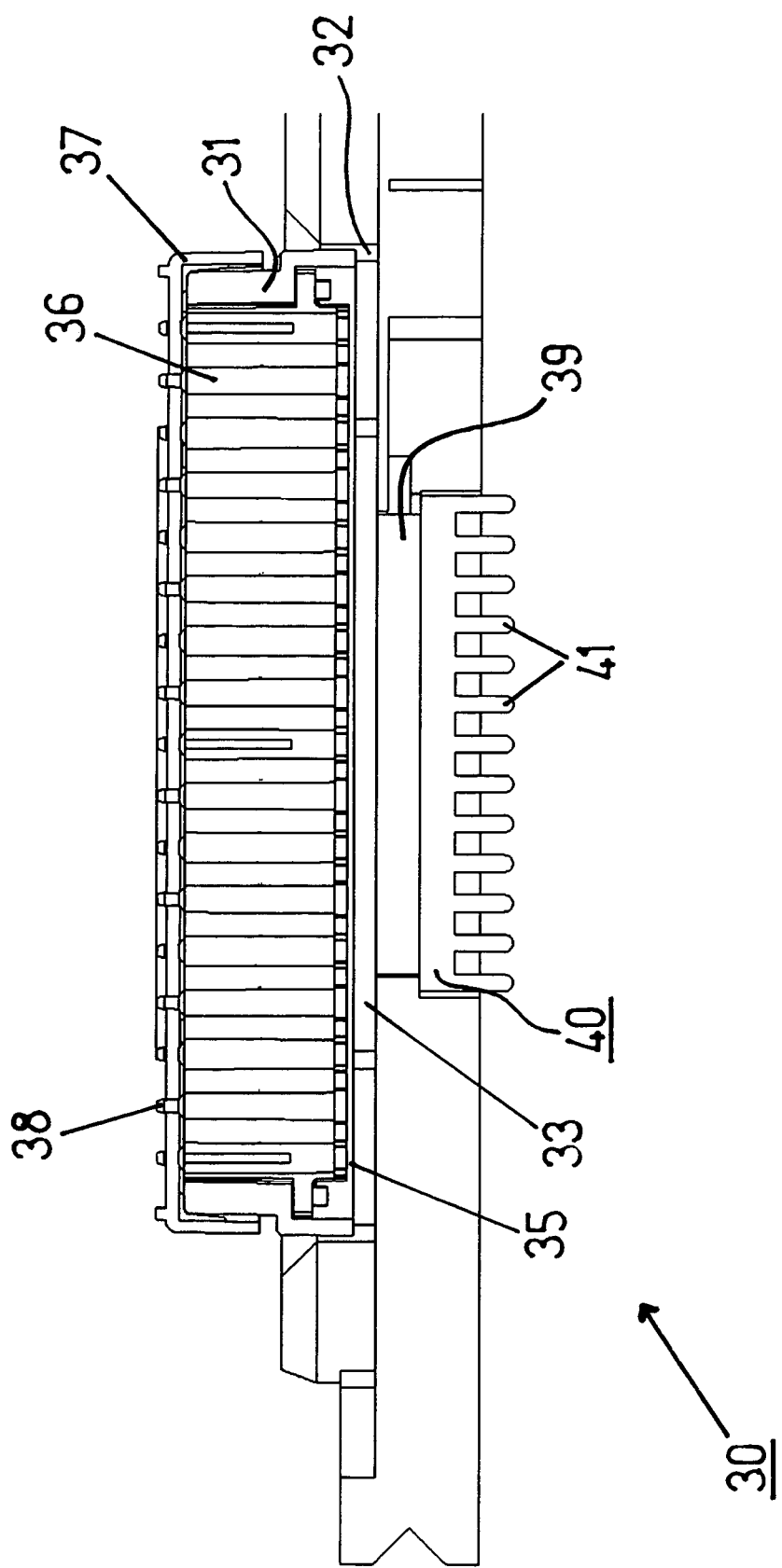
FIG. 6 shows a schematic side view of a form of embodiment of a device according to the invention with a container and a cooling appliance.

FIG. 6 shows a schematic side view of a form of embodiment of a device 30 according to the invention for making electrical contact with at least one container 31 fitted with electrodes 36, the container being fitted with a cover 37 through which the contact elements 38, with which the electrodes 36 are fitted, project upwards. The device 30 comprises at least one receptacle 32 onto which the container 31 can be set. The receptacle 32 is fitted with a cooling appliance 33, which in the present example of embodiment is a Peltier element. In the form of embodiment represented here the cooling appliance is connected with a heat conductor 39 and a heat exchanger 40. The heat exchanger 40 provides for the efficient removal of the heat generated in the container 31 and transported through the cooling appliance 33 via the heat conductor 39, into the environment. In the example represented the heat exchanger 40 is a body fitted with cooling fins 41. To increase the removal of the heat generated in the process the device 30 can also be fitted with a ventilator (not represented). When making contact with the contact elements 38 of the electrodes 36 the contact means of the contact appliance (not represented) exert a vertical pressure onto the container 31. In order that this one-sided pressure does not lead to tilting of the container 31, the device 30 according to the invention can in an advantageous embodiment of the invention comprise a least one pressure application appliance, not represented here, which presses the container 31 evenly onto the receptacle 32 and the cooling appliance 33. The pressure application appliance can be designed in the form of a frame and can be set upon at least one part of the edge of the container 31. The pressure application appliance can also be part of the contact appliance. In particular the pressure application appliance serves to displace the air from the clearance 35 between the container 31 and the receptacle 32, in order to intensify the contact between the electrodes of the container 31 and the cooling appliance 33. In this manner effective cooling of the container 31 and the electrodes can be ensured.

Figure 7:
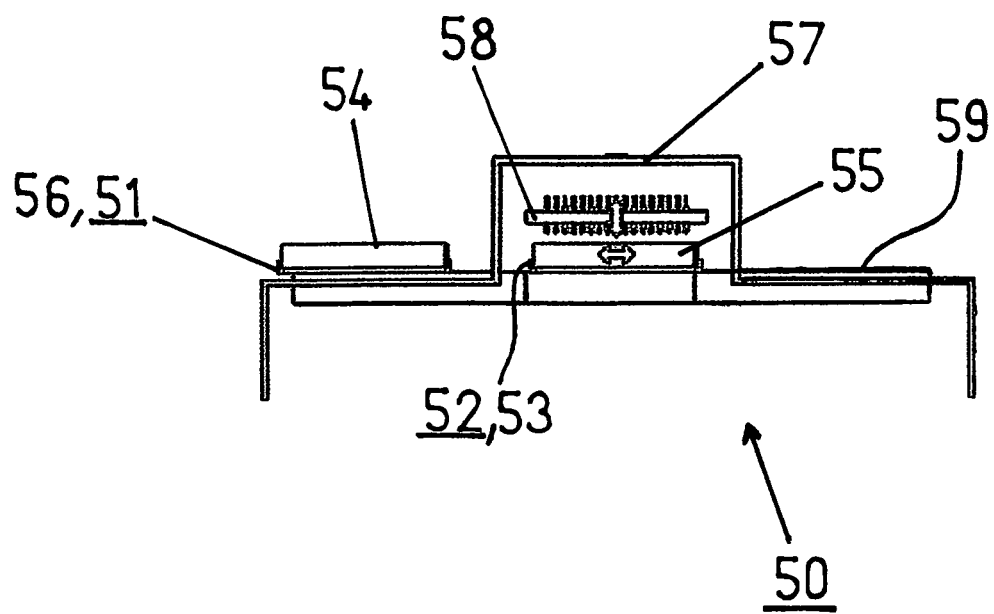
FIG. 7 shows a schematic side view of a further form of embodiment of a device according to the invention with linear movement of two receptacles.

FIG. 7 shows a schematic side view of a further form of embodiment of a device 50 according to the invention with linear movement of the receptacles. The device 50 comprises two receptacles 51, 52, upon each of which a container 54, 55 is set. The receptacle 52 is located in this representation inside a housing 57 on the central position 53 and is arranged below a contact appliance 58. By means of the contact appliance 58 electrical contact can be made with the electrodes, not represented here, of the container 55 by means of a vertical movement of the contact appliance 58, in order to apply one or a plurality of voltage pulses to the reaction volumes of the container 55. The receptacle 51 is arranged outside the housing on the left-hand position 56, this position 56 serving to provide the preparation or post-processing of the container 54. Moreover a further position 59 is located on the opposite side of the housing 57, which provides space for the contact appliance 55 and the preparation and/or post-processing of the container 55. In this exemplary form of embodiment of the invention the positions of the containers can be exchanged by means of coupled or decoupled linear movements. The exchange of the container positions can here be achieved by either a movement of the containers themselves, or a movement of the receptacles. The device 50 according to the invention therefore comprises two receptacles 51, 52, each of which can assume two positions, 53 or 56, or 53 or 59, respectively (in total three positions 53, 56, 59 are provided). The receptacle 51 can thereby be linearly moved between the left-hand position 56 and the central position 53, while the receptacle 52 can be moved between the central position 53 and the right-hand position 59. This configuration always enables the container that should be the next to be subjected to the electrical treatment to be transported into the housing 57 (position 53). During the electrical treatment the other container is then accessible outside the housing 57 for the preparation and/or post-processing (positions 56 and 59).

REFERENCE SYMBOL LIST

1 Device
2 Housing
3 Receptacle
4 Container
5 Plate
6 Turntable
7 Receptacle
8 Contact appliance
9 Yoke
10 Yoke
11 Rail
12 Rail
13 Distribution appliance
14 Cover plate
15 Container
16 Axle
17 Contact means
20 Device
21 Receptacle
22 Container
23 Distribution appliance
24 Contact means
25 Contact appliance
26 Contact element
30 Device
31 Container
32 Receptacle
33 Cooling appliance
34 Arrow
35 Clearance
36 Electrode
37 Cover
38 Contact element
39 Heat conductor
40 Heat exchanger
41 Cooling fins
50 Device
51 Receptacle
52 Receptacle
53 Position
54 Container
55 Container
56 Position
57 Housing
58 Contact appliance
59 Position.

The invention claimed is:

1. A device for making electrical contact with at least two containers fitted with electrodes, comprising
at least a first and a second receptacle configured so that upon each of them at least one of said containers can be placed, and
at least one contact appliance configured to make an electrical contact with the electrodes of the at least two containers fitted with electrodes, wherein the first receptacle is located at or inside the contact appliance, and the first and the second receptacle are configured to be moved such that after completion of the movement, positions of the first and second receptacle are exchanged and the second receptacle is located at or inside the contact appliance, and wherein the contact appliance is arranged inside a housing and the receptacles are arranged on a moveable plate, one part of said moveable plate and at least one receptacle being arranged inside said housing and another part of said moveable plate and at least one other receptacle being arranged outside said housing.

2. The device according to claim 1, wherein at least one of said at least two containers comprises at least two reaction volumes each fitted with at least one electrode, wherein the at least one contact appliance comprises at least one contact unit, wherein the number of contact units is less than the number of reaction volumes, wherein the at least one contact unit has contact means for making contact with the electrodes of the at least two reaction volumes.

3. The device according to claim 2, wherein the contact appliance is designed as a support and is configured to be essentially moved approximately parallel to a plane of contact.

4. The device according to claim 2, wherein at least one part of the contact appliance is configured to be moved approximately at right-angles to a plane of contact.

5. The device according to claim 2, wherein at least one receptacle is fitted with a cooling appliance.

6. The device according to claim 5, wherein the cooling appliance comprises at least one Peltier element.

7. The device according to claim 5, wherein at least one pressure application appliance is provided, which presses the container onto the receptacle and/or the cooling appliance.

8. The device according to claim 2, wherein the contact appliance is a bridge and/or slide and is configured to be essentially be moved approximately parallel to a plane of contact.

9. The device according to claim 1, wherein the at least one container is a multi-well plate.

10. The device according to claim 1, wherein at least one of said at least two containers comprises at least two reaction volumes each fitted with at least one electrode.

11. The device according to claim 1, wherein the at least one contact appliance comprises at least one contact unit, which has contact means for making contact with the electrodes of said at least two containers.

12. The device according to claim 1, wherein the moveable plate is a turntable.

13. The device according to claim 1, wherein the receptacles are located below the contact appliance.

14. The device according to claim 13, wherein the contact appliance is designed as a slide and/or bridge.

* * * * *